United States Patent [19]

Hater et al.

[11] Patent Number: Plant 7,688

[45] Date of Patent: Oct. 29, 1991

[54] ROSE PLANT NAMED 'SWEET SUCCESS'

[76] Inventors: Gary R. Hater, 4286 Turf La., Cincinnati, Ohio 45202; John D. Pottschmidt, 5584 Palisades Dr., Cincinnati, Ohio 45238

[21] Appl. No.: 483,540

[22] Filed: Feb. 22, 1990

[51] Int. Cl.[5] ..... A01H 5/00

[52] U.S. Cl. ..... Plt./18

[58] Field of Search ..... Plt. 18

*Primary Examiner*—James R. Feyrer

*Attorney, Agent, or Firm*—Ronald J. Snyder

[57] ABSTRACT

A new hybrid tea rose plant is provided as developed from a seedling in a direct effort to breed a new variety. The new rose plant resulted from the crossing of parent varieties of Chablis and Pristine and features a vigorous growing habit, an ability to yield abundant blooms on an almost continuous basis, and distinctive coloration changing from beige at the base of petal to a light pink on both sides of the petal. High resistance to blackspot is also exhibited.

2 Drawing Sheets

SUMMARY OF THE INVENTION

The present invention relates to a new and distinct variety of rose plant of the hybrid tea class which was originated by crossing two known varieties, namely Chablis and Pristine. It is contemplated that the variety will be marketed under the American Rose Society, (ARS) registered name of Sweet Success. Color descriptions are made in reference to The Royal Horticultural Society Colour Chart and the color plates are indicated by number (e.g. 62D).

Artificial pollination was undertaken and the new rose plant was developed from a seedling with the primary objective of breeding a new variety of rose plant with the ability to yield on an almost continuous basis abundant blooms with a large number of petals. These objectives were substantially achieved along with other desirable improvements as evidenced in the detailed description below. The new hybrid tea rose plant of the present invention was bred in 1985, and the resultant seedling was propagated in the winter of 1986.

BRIEF DESCRIPTION OF THE PHOTOGRAPHS AND DRAWINGS

The accompanying photographs show typical specimens of the vegetative growth and flowers of this new variety and its distinguishing combination of characteristics, with the photographs being depicted in color as nearly true as it is reasonably possible to make the same in color illustrations of this character. The rose plants of the new variety described herein were grown outdoors at Cincinnati, Ohio.

DETAILED DESCRIPTION

The following description is based on specimens of the new variety of rose plant grown outdoors at Cincinnati, Ohio.

Type: Hardy; outdoor; bush; for exhibition, cut flowers and garden decoration.

Class: Hybrid Tea.

Propagation: Maintains its distinguishing characteristics through successive propagations as budded plants, rooted cuttings, and grafting.

FLOWER:

Locality where grown: Cincinnati, Ohio.

Flowers borne: Singly, on long stems, occasionally with side buds.

Quantity of Bloom: Abundant outdoors, in Cincinnati, 4 to 5 cycles per season.

Continuity: Almost continuous.

Fragrance: Slight, tea.

Bud:

*Peduncle.*—Medium long, green (143C), erect stiff, significant prickles which are randomly spaced. Illustrated in FIG. 6.

*Before the calyx breaks.*—Size-medium. Form ovoid.

Figure 1:
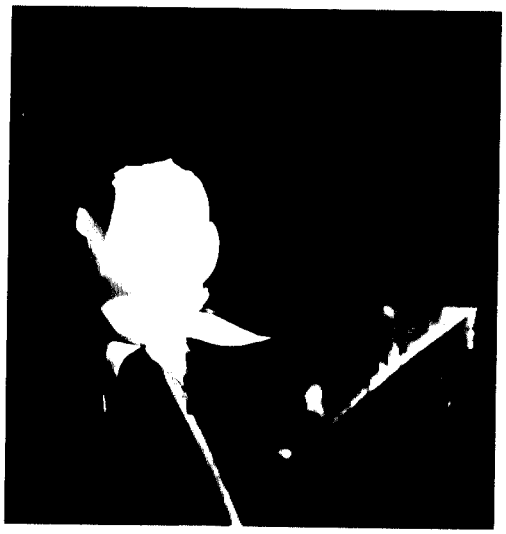
FIG. 1 illustrates a specimen of a flowering bud as calyx breaks.

*As calyx breaks.*—Light pink (62D) with a flush of dark pink (63D). Edge of many of the petals have a red purple (61C) pigmentation. Illustrated in FIG. 1.

Bloom:

*Size when fully open.*—Medium —four to five and one half inches.

*Petalage.*—Very double; from fifty six to sixty four petals arranged regularly.

Figure 2:
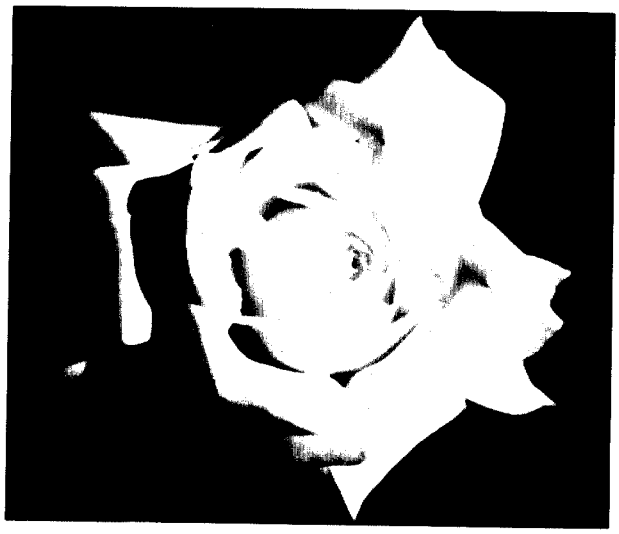
FIG. 2 illustrates a specimen of an open flower—plan view—obverse.
Figure 3:
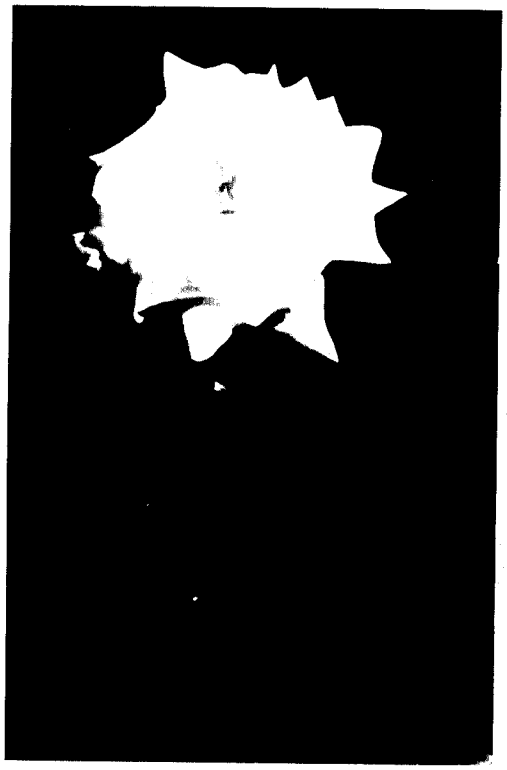
FIG. 3 illustrates a specimen of a flower in full open stage, as well as the characteristic mature green foliage and its dark red serrated edges.
Figure 4:
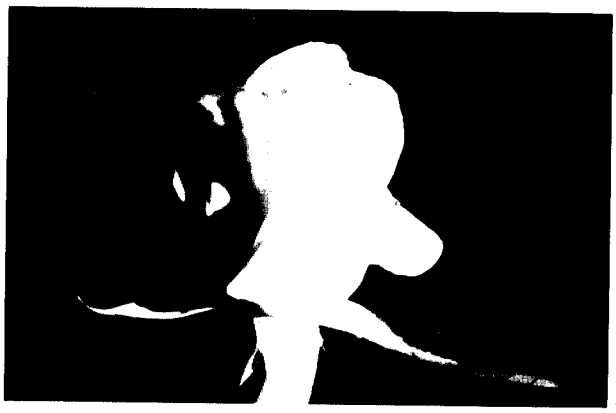
FIG. 4 illustrates a specimen of a flowering bud as the sepals open, showing the underside of the petals and the characteristic coloration thereof.

*Form.*—Cupped, high centered; globular at first and becoming high centered. Mature petals are highly recurved, as illustrated in FIG. 2. Center remains tight while outer petals become recurved and regularly spaced. In the full open stage the bloom has evenly spaced petals with Zinnia-like form, as illustrated in FIG. 3.

Petals: Leathery with a satiny shine inside and outside.

*Shape.*—Scalloped outer edge that is weather dependant. No apparent notches and the petals are generaly oval, and recurved.

Figure 5:
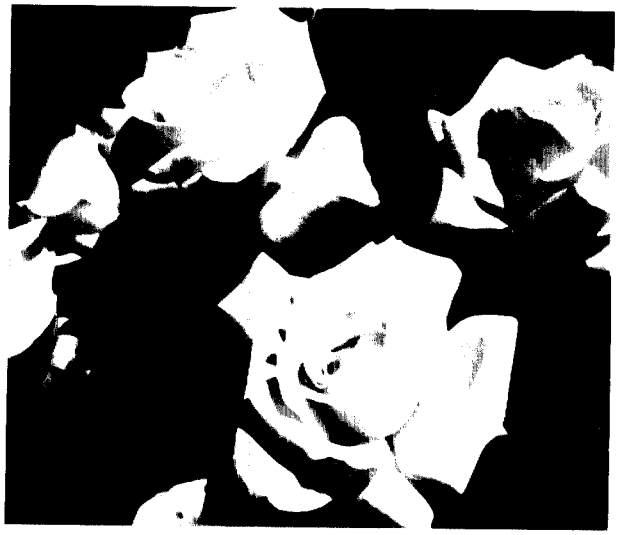
FIG. 5 illustrates a specimen of a cluster of flowers showing a bud at the opening of the sepals and buds and blossoms at various stages of opening.

*Color.*—Yellow (13C) at the base changing to a coral (37C) on the inside, followed by light pink (62D) on both sides of the petal. The edge often acquires a dark pink (63D) edge in temperatures greater than ninety degrees Fahrenheit. In cooler weather, with nights less than forty five degrees Fahrenheit, the petals are almost completely white and retain only a hint of pink pigment, as illustrated in FIG. 5. The color tends to lighten as the bloom becomes full, and colors are generally move vivid in fall season.

*General color effect.*—Light Pink Inflorescence with a dark pink edge when fresh.

*Behavior.*—Drop off cleanly; do not fade.

*Flower longevity.*—On the bush five to seven days in September. As a cut flower it remains fresh for at least three days at room temperature. The above color description is taken from fifty bushes grown in Cincinnati, Ohio.

REPRODUCTIVE ORGANS

Figure 6:
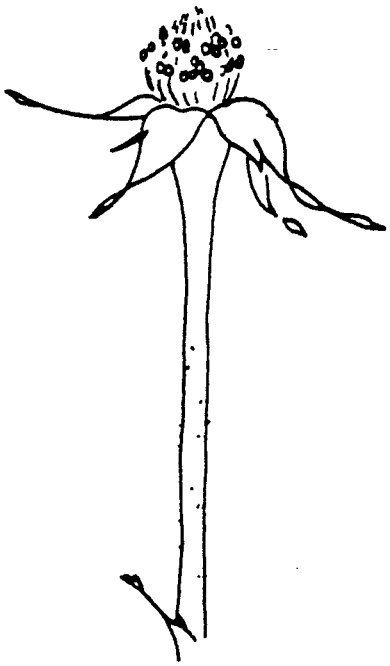
FIG. 6 is a drawing illustrating a specimen of the peduncle and reproductive organs of the new rose plant of the subject invention.
Figure 7:
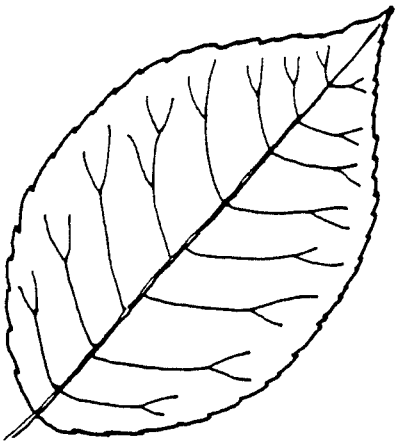
FIG. 7 is a drawing illustrating the characteristic leaflets of the foliage.

Stamens: Many, arranged irregularly.
Filaments: Many, varied, red (45A).
Anthers: Small to medium size, yellow (19A).
Pollen: Yellow, moderate.
Pistils: Many.
Stigma: Straw Yellow (19B).
Ovaries: All enclosed in the calyx.
Hips: Pointed at the base, becoming ovoid; smooth sides, as illustrated in FIG. 6.
Sepals: Pointed, spear shaped and highly recurved.
Seeds: Large, number similar to Pristine in number.

PLANT

Foliage:

*Leaves.*—Compound of five leaflets; normal; large; very glossy; waxy.

*Leaflets.*—Ovoid with apex acute; base round; margin serrate (3).

*Color.*—Mature — dark green (131A), often while maturing venation and serrated edges are dark red, as illustrated in FIG. 3. Underside is transparent red (60C) with green showing through.

Figure 8:
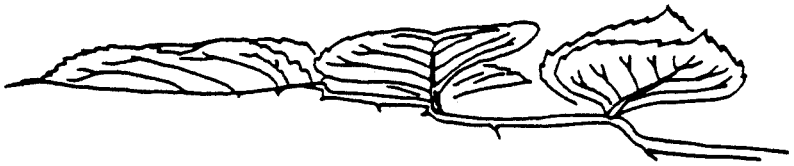
FIG. 8 illustrates the underside of typical foliage of the new rose plant.

*Rachis.*—Medium heavy; upper side smooth, underside thorny, as illustrated in FIG. 8.

*Stipules.*—Medium long; medium wide and reddish in color.

*Disease.*—Very resistant to blackspot and to lesser extent mildew.

Growth:

*Habit.*—Upright, moderately branched.

*Growth.*—Vigorous, tall to six feet in height.

Figure 9:
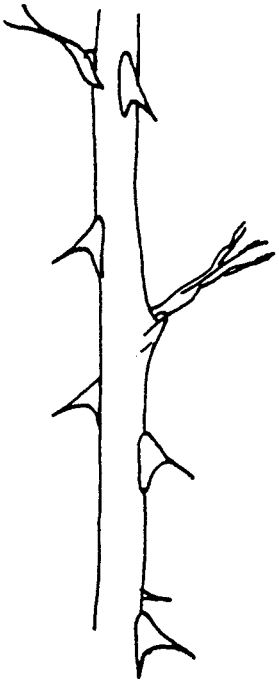
FIG. 9 illustrates a typical main stem.
Figure 10:
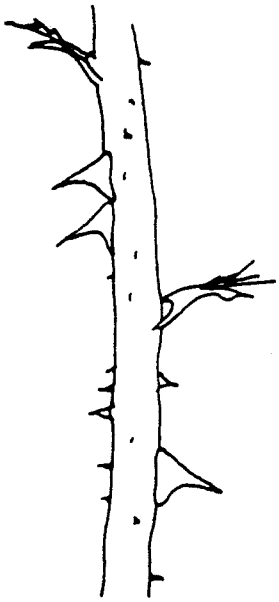
FIG. 10 illustrates a specimen of a main stem whic occasionally occurs in the new rose plants of the subject invention.

*Main stems.*—Medium green. Thorns: Long, pointed slightly downward and generally bright red, as illustrated in FIG. 9. Prickles: Generally Absent. (See FIG. 9). Hairs: None. Occasionally a unique thorn/prickle pattern appears in which the thorns are found in clusters while the prickles are on the opposite side of the stem, as illustrated in FIG. 10. This thorn/prickle pattern may be completely unique.

We claim:

1. A new and distinct variety of rose plant of the hybrid tea class, characterized as to novelty by its vigorous growing habit, its ability to yield on an almost continuous basis abundant blooms, and quality and color of its bloom and foliage as shown and described.

* * * * *